US008704013B2

(12) United States Patent
Jevtic et al.

(10) Patent No.: US 8,704,013 B2
(45) Date of Patent: Apr. 22, 2014

(54) INTEGRATED PROCESS FOR PRODUCING ETHANOL

(75) Inventors: Radmila Jevtic, Pasadena, TX (US); Victor J. Johnston, Houston, TX (US); David Lee, Seabrook, TX (US); Adam Orosco, Houston, TX (US); Lincoln Sarager, Houston, TX (US); Mark O. Scates, Houston, TX (US); James H. Zink, League City, TX (US)

(73) Assignee: Celanese International Corporation, Dallas, TX (US)

( * ) Notice: Subject to any disclaimer, the term of this patent is extended or adjusted under 35 U.S.C. 154(b) by 126 days.

(21) Appl. No.: 13/292,848

(22) Filed: Nov. 9, 2011

(65) Prior Publication Data

US 2013/0116479 A1    May 9, 2013

(51) Int. Cl.
*C07C 27/04*    (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS

| | | |
|---|---|---|
| 2,607,807 A | 8/1952 | Ford |
| 2,882,244 A | 4/1959 | Milton |
| 3,102,150 A | 8/1963 | Hunter et al. |
| 3,130,007 A | 4/1964 | Breck |
| 3,478,112 A | 11/1969 | Karl et al. |
| 3,769,329 A | 10/1973 | Paulik et al. |
| 3,990,952 A | 11/1976 | Katzen et al. |
| 4,126,539 A | 11/1978 | Derr, Jr. et al. |
| 4,149,940 A | 4/1979 | Pinto |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,443,639 A | 4/1984 | Pesa et al. |
| 4,454,358 A | 6/1984 | Kummer et al. |
| 4,497,967 A | 2/1985 | Wan |
| 4,517,391 A | 5/1985 | Schuster et al. |
| 4,569,726 A | 2/1986 | Berg et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,414,161 A | 5/1995 | Uhm et al. |
| 5,415,741 A | 5/1995 | Berg |
| RE35,377 E | 11/1996 | Steinberg et al. |
| 5,599,976 A | 2/1997 | Scates et al. |
| 5,762,765 A | 6/1998 | Berg |
| 5,821,111 A | 10/1998 | Grady et al. |
| 5,993,610 A | 11/1999 | Berg |
| 6,143,930 A | 11/2000 | Singh et al. |
| 6,232,352 B1 | 5/2001 | Vidalin et al. |
| 6,326,515 B1 | 12/2001 | Clode et al. |
| 6,339,171 B1 | 1/2002 | Singh et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,657,078 B2 | 12/2003 | Scates et al. |
| 6,685,754 B2 | 2/2004 | Kindig et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,208,624 B2 | 4/2007 | Scates et al. |
| 7,223,886 B2 | 5/2007 | Scates et al. |
| 7,297,236 B1 | 11/2007 | Vander Griend et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,608,744 B1 | 10/2009 | Johnston et al. |

(Continued)

FOREIGN PATENT DOCUMENTS

| | | |
|---|---|---|
| CN | 102228831 | 11/2011 |
| CN | 102229520 | 11/2011 |

(Continued)

OTHER PUBLICATIONS

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

(Continued)

*Primary Examiner* — Johann R Richter
*Assistant Examiner* — Kofi Adzamli

(57) ABSTRACT

In one embodiment, the invention is to a process for producing ethanol, the process comprising the steps of carbonylating methanol in a carbonylation system in the presence of a carbonylation catalyst under conditions effective to form acetic acid; hydrogenating the acetic acid in a hydrogenation system in the presence of a hydrogenation catalyst to form a crude ethanol product comprising ethanol and water; separating the ethanol from the water to form an ethanol stream and a water stream; and directing at least a portion of the water stream to the carbonylation system, e.g., for use as an extractant in a permanganate reducing compound removal system.

17 Claims, 5 Drawing Sheets

(56) References Cited

U.S. PATENT DOCUMENTS

| | | |
|---|---|---|
| 7,682,812 B2 | 3/2010 | Verser et al. |
| 7,700,814 B2 | 4/2010 | Garton et al. |
| 7,834,223 B2 | 11/2010 | Atkins et al. |
| 7,842,844 B2 | 11/2010 | Atkins |
| 7,855,306 B2 | 12/2010 | Zinobile et al. |
| 7,863,489 B2 | 1/2011 | Johnston et al. |
| 7,884,253 B2 | 2/2011 | Stites et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0077771 A1 | 4/2003 | Verser et al. |
| 2004/0122257 A1 | 6/2004 | Cheung et al. |
| 2006/0019360 A1 | 1/2006 | Verser et al. |
| 2007/0031954 A1 | 2/2007 | Mairal et al. |
| 2007/0270511 A1 | 11/2007 | Melnichuk et al. |
| 2008/0103335 A1 * | 5/2008 | Scates et al. ............ 562/606 |
| 2008/0207953 A1 | 8/2008 | Houssin et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0166172 A1 | 7/2009 | Casey et al. |
| 2009/0221725 A1 | 9/2009 | Chorney et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |

FOREIGN PATENT DOCUMENTS

| | | | |
|---|---|---|---|
| DE | 19914260 | 10/2000 | |
| EP | 0056488 | 7/1982 | |
| EP | 0104197 | 4/1984 | |
| EP | 0167300 | 1/1986 | |
| EP | 0175558 | 3/1986 | |
| EP | 0192587 | 8/1986 | |
| EP | 0198682 | 10/1986 | |
| EP | 0285420 | 10/1988 | |
| EP | 0285786 | 10/1988 | |
| EP | 0456647 | 11/1991 | |
| EP | 2060553 | 5/2009 | |
| EP | 2060555 | 5/2009 | |
| EP | 2072487 | 6/2009 | |
| EP | 2072488 | 6/2009 | |
| EP | 2072489 | 6/2009 | |
| EP | 2072492 | 6/2009 | |
| EP | 2186787 | 5/2010 | |
| JP | 6-116182 | 4/1994 | |
| JP | 2001-046874 | 2/2001 | |
| WO | WO 83/03409 | 10/1983 | |
| WO | WO 02/092541 | 11/2002 | |
| WO | WO 2005/102513 | 11/2005 | |
| WO | WO 2007/003897 | 1/2007 | |
| WO | WO 2009/009320 | 1/2009 | |
| WO | WO 2009/063176 | 5/2009 | |
| WO | WO 2009/063176 A1 * | 5/2009 | ........... C07C 29/149 |
| WO | WO 2009063176 A1 * | 5/2009 | |
| WO | WO 2009/105860 | 9/2009 | |
| WO | WO 2010/055285 | 5/2010 | |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2011/060003 mailed Sep. 10, 2012.

* cited by examiner

INTEGRATED PROCESS FOR PRODUCING ETHANOL

FIELD OF THE INVENTION

The present invention relates generally to processes for producing ethanol. In particular, the invention relates to processes for producing ethanol from methanol via an acetic acid intermediate, in which water formed in the ethanol synthesis step is recycled to the acetic acid synthesis step.

BACKGROUND OF THE INVENTION

Ethanol for industrial use is conventionally produced from petrochemical feed stocks, such as oil, natural gas, or coal; from feed stock intermediates, such as syngas; or from starchy materials or cellulose materials, such as corn and sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are often converted to ethanol by fermentation. However, fermentation is typically used for consumer production of ethanol. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. In the reduction of an alkanoic acid, such as acetic acid, water may be formed in an equal molar ratio with ethanol. The need exists for uses for the excess water that is formed in the ethanol production process. The need also exists for integrated processes for making ethanol from methanol.

SUMMARY OF THE INVENTION

The present invention is directed to integrated processes for forming ethanol from methanol, preferably through an acetic acid intermediate.

In one embodiment, the invention is to a process for producing a water stream. The process comprises the step of hydrogenating an acetic acid feed stream to form a crude ethanol product. The crude ethanol product preferably comprises ethanol, water, ethyl acetate, and acetic acid. The process further comprises the step of separating at least a portion of the crude ethanol product in at least one column into a distillate comprising ethanol and a residue comprising the water stream. The water is directed to an acetic acid production process, preferably for use as an extractant for removing permanganate reducing compounds (PRC's) such as acetaldehyde from a process stream contained in said acetic acid production process.

In another embodiment, the invention is to a process for carbonylating methanol in a carbonylation system in the presence of a carbonylation catalyst under conditions effective to form acetic acid; hydrogenating the acetic acid in a hydrogenation system in the presence of a hydrogenation catalyst to form a crude ethanol product comprising ethanol and water; separating the ethanol from the water to form an ethanol stream and a water stream; and directing at least a portion of the water stream to the carbonylation system.

In yet another embodiment, the invention is to a process for reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst; hydrogenating the acetic acid in a hydrogenation system in the presence of a hydrogenation catalyst to form a crude ethanol product comprising ethanol and water, separating the ethanol from the water to form an ethanol stream and a water stream, and directing at least a portion of the water stream to the carbonylation system.

In yet another embodiment, the invention is to a process for producing a water stream, the process comprising providing a crude ethanol product comprising ethanol, water, ethyl acetate, and acetic acid, separating at least a portion of the crude ethanol product into an ethanol stream and a water stream, wherein the water stream is essentially free of organic impurities other than acetic acid, and directing at least a portion of the water stream to a carbonylation system.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to integrated processes for making ethanol from methanol. In one embodiment, the process includes a step of carbonylating methanol in a carbonylation system in the presence of a carbonylation catalyst under conditions effective to form acetic acid. The acetic acid is subsequently hydrogenated in a hydrogenation system in the presence of a hydrogenation catalyst to form a crude ethanol product comprising ethanol and water. The crude ethanol product is separated into an ethanol stream and a water stream. At least a portion of the water stream is then directed back to the carbonylation system. In a preferred embodiment, at least a portion of the water stream is used as an extractant in the carbonylation system, preferably as an extractant for removing permanganate reducing compounds (PRC's) such as acetaldehyde from one or more process streams in the carbonylation system.

Figure 1:
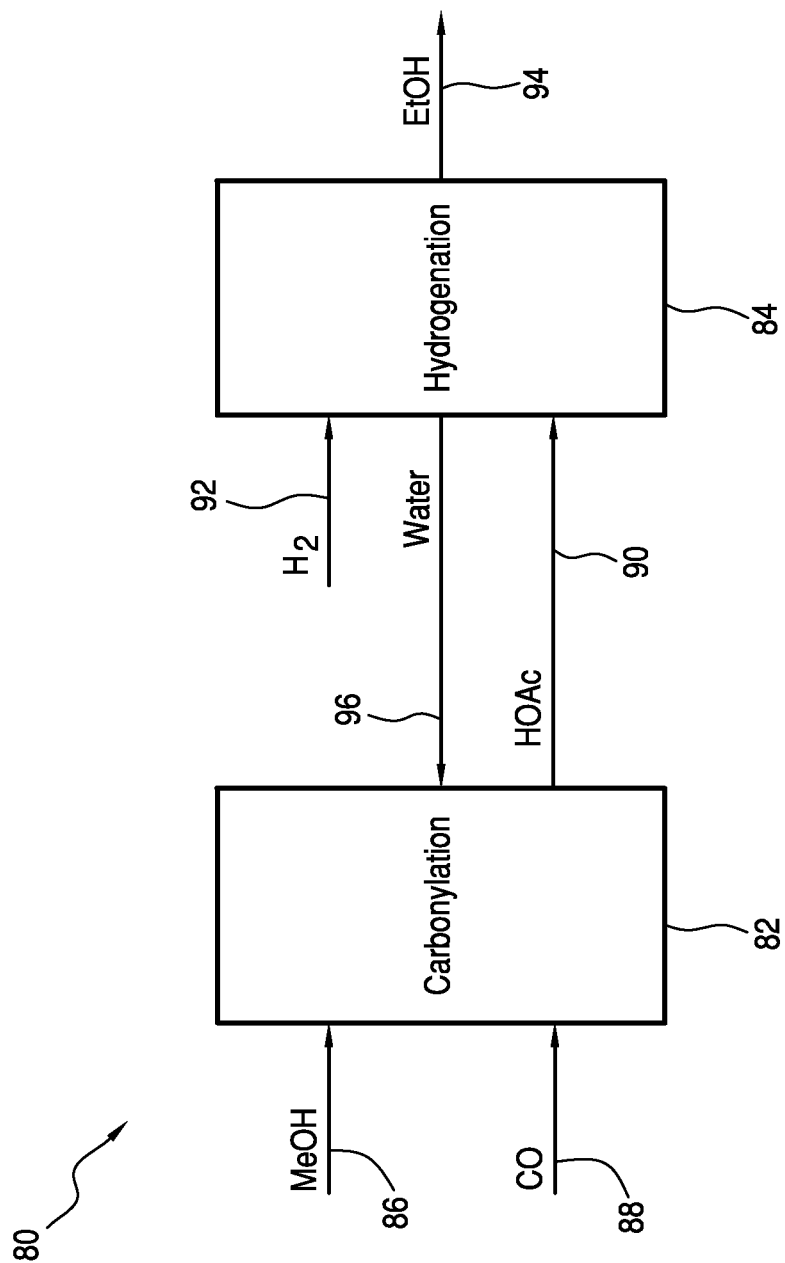
FIG. 1 is a schematic diagram of an integrated system for forming ethanol from methanol via an acetic acid intermediate in accordance with one embodiment of the present invention.

FIG. 1 illustrates an integrated process 80 in accordance with one embodiment of the present invention. Process 80 comprises carbonylation system 82 and hydrogenation system 84. Carbonylation system 82 receives methanol feed 86 and carbon monoxide feed 88. The methanol and the carbon monoxide are reacted in carbonylation system 82 to form acetic acid. Carbonylation system 82, in some embodiments, further comprises a purification train comprising one or more distillation columns and/or extraction units (not shown in FIG. 1) to separate crude acetic acid into an acetic acid product stream 90.

Acetic acid product stream 90 is fed, more preferably directly fed, to hydrogenation system 84. Hydrogenation system 84 also receives hydrogen feed 92. In hydrogenation system 84, the acetic acid in acetic acid product stream 90 is hydrogenated to form a crude ethanol product comprising ethanol and other compounds such as water, ethyl acetate, and unreacted acetic acid. Hydrogenation system 84 further comprises one or more separation units, e.g., distillation columns and/or extraction units (not shown in FIG. 1.), for separately recovering ethanol and water from the crude ethanol product. An ethanol product stream 94 is then recovered from hydrogenation system 84. As shown, water that is recovered from the hydrogenation system is directed to the carbonylation system, as shown by water stream 96, where it may be used, for example, as an extraction agent for the removal of PRC's from one or more process streams in carbonylation system 82. In a preferred embodiment, the water stream 96 is used as an extraction unit for separating acetaldehyde from one or more process streams in carbonylation system 82.

In addition to integrating the water stream between the hydrogenation system 84 and carbonylation system 82, the process may also be integrated with methods for producing acetic acid and/or methods for producing methanol. For example, acetic acid may be produced from methanol, and thus ethanol production according to embodiments of the present invention may be produced from methanol. In one embodiment, the present invention comprises producing methanol from syngas, carbonylating the methanol to form acetic acid, and reducing acetic acid to form an alcohol, namely ethanol. In still another embodiment, the present invention comprises producing ethanol from a carbon source, such as coal, biomass, petroleum, or natural gas, by converting the carbon source to syngas, followed by converting the syngas to methanol, carbonylating the methanol to form acetic acid, and reducing acetic acid to form ethanol. In still another embodiment, the present invention comprises producing ethanol from a carbon source, such as coal, biomass, petroleum, or natural gas, by converting the carbon source to syngas, separating the syngas into a hydrogen stream and a carbon monoxide stream, carbonylating a methanol with the carbon monoxide stream to form acetic acid, and reducing acetic acid to form an ethanol. In addition, methanol may be produced from the syngas.

Various carbonylation systems and hydrogenation systems may be used in the processes of the present invention. Exemplary materials, catalysts, reaction conditions, and separation processes that may be used in the carbonylation and hydrogenation systems employed in the present invention are described further below.

Carbonylation System

In the carbonylation process, methanol is reacted with carbon monoxide in the presence of a carbonylation reactor under conditions effective to form acetic acid. In some embodiments, some or all of the raw materials for the carbonylation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol mixture, as described in further detail below, may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with the hydrogenation system as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The carbonylation of methanol, or another carbonylatable reactant, including, but not limited to, methyl acetate, methyl formate, dimethyl ether, or mixtures thereof, to acetic acid preferably occurs in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259, the entirety of which is incorporated herein by reference.

Without being bound by theory, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The halogen-containing catalyst promoter of the catalyst system comprises a halogen compound, typically an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at concentrations well below that which has heretofore been thought practical for achieving sufficient reaction rates. It has previously been taught that in rhodium-catalyzed carbonylation reactions of the type set forth in this invention, the addition of water exerts a beneficial effect upon the reaction rate. See, e.g., U.S. Pat. No. 3,769,329, incorporated herein by reference in its entirety. Thus, commercial operations are commonly run at water concentrations of at least about 14 wt. %. Accordingly, it has been quite unexpected that reaction rates substantially equal to and above reaction rates obtained with such comparatively high levels of water concentration can be achieved with water concentrations below 14 wt. % and as low as about 0.1 wt. %.

In accordance with the carbonylation process most useful to manufacture acetic acid according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously. See, e.g., U.S. Pat. No. 5,001,259, incorporated herein by reference in its entirety. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process most useful in this invention, the additional iodide ion over and above the iodide ion present as hydrogen iodide is generally present in the catalyst solution in amounts such that the total iodide ion concentration is from about 2 to about 20 wt. % and the methyl acetate is generally present in amounts of from about 0.5 to about 30 wt. %, and the methyl iodide is generally present in amounts of from about 5 to about 20 wt. %. The rhodium catalyst is generally present in amounts of from about 200 to about 2000 parts per million (ppm).

Typical reaction temperatures for carbonylation will be from 150 to 250° C., with the temperature range of 180 to 220° C. being a preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

In the carbonylation of methanol, PRC's such as acetaldehyde and PRC precursors may be formed as a byproduct, and as a result, the carbonylation system preferably includes a PRC Removal System (PRS) for removing such PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. Thus, in some embodiments, the invention relates to processes for reducing and/or removing PRC's or their precursors from intermediate streams during the formation of acetic acid by said carbonylation processes.

In particular, the present invention relates to a process in which a condensed light phase from a light ends column overhead is subjected to a distillation step to obtain an overhead that is subjected to a water extraction step to selectively reduce and/or remove PRC's from the process. In one embodiment, the distillation step in the PRS includes a single distillation column as described in U.S. Pat. No. 7,855,306, the entirety of which is incorporated herein by reference, while in other embodiments the distillation step may include two or more distillation steps as described, for example, in U.S. Pat. No. 6,143,930, the entirety of which is incorporated herein by reference. Similarly, in one embodiment, the extraction step in the PRS includes a single extraction unit, while in other embodiments, multiple extraction units employing the same or different extractants, may be employed, as described for example, in U.S. Pat. No. 7,223,886, the entirety of which is incorporated herein by reference. Although the PRS is illustrated and described herein as having a single distillation column and a single extraction unit, it should be understood that the principles of the invention may be employed with separation systems having multiple distillation columns and/or multiple extraction units.

Figure 2:
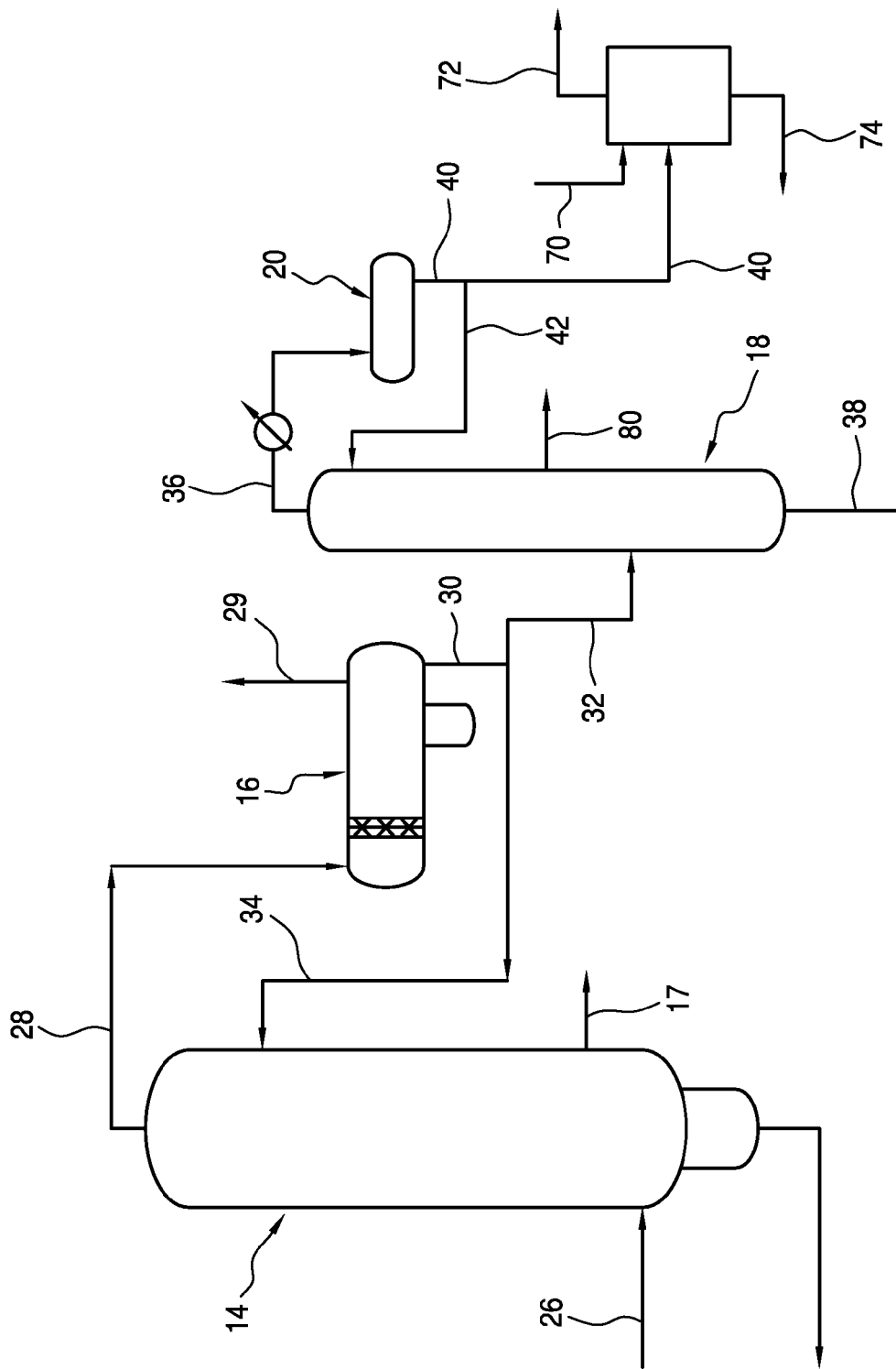
FIG. 2 is a schematic diagram of an acetic acid separation system, which includes a permanganate reducing compound removal system, in accordance with one embodiment of the present invention.

A typical reaction and acetic acid recovery system that is used for the iodide-promoted rhodium catalyzed carbonylation of methanol to acetic acid is shown in FIG. 2 and includes a liquid phase carbonylation reactor, flasher, and a light ends column 14. In the process, carbonylation product obtained in the reactor (not shown) is provided to the flasher (not shown) where a volatile ("vapor") overhead stream 26 comprising acetic acid and a less volatile catalyst phase (not shown), comprising a catalyst-containing solution are obtained. The volatile overhead stream 26 comprising acetic acid is provided to the light ends column 14 where distillation yields a purified acetic acid product that is removed via sidestream 17 and an overhead distillate stream 28 (hereafter "low-boiling overhead vapor stream"). Acetic acid removed via sidestream 17 can be subjected to further purification, such as to a drying column (not shown) for selective separation of acetic acid from water. In a preferred embodiment, acetic acid derived from sidestream 17, optionally after processing in one or more additional separation units, e.g., drying column and/or resin guard beds, is directed to the hydrogenation system, described below, where it is reduced with hydrogen in the presence of a hydrogenation catalyst under conditions effective to form ethanol.

As they constitute standard equipment, well known in the art, the reactor and flasher are not shown in FIG. 2. The carbonylation reactor is typically either a stirred vessel or bubble-column type within which the reacting liquid or slurry contents are maintained automatically at a constant level. Into this reactor, fresh methanol, carbon monoxide and sufficient water as needed to maintain at least a finite concentration of water in the reaction medium are continuously introduced. Also introduced into the reactor is a recycled catalyst solution, such as from the flasher base, a recycled methyl iodide phase, a recycled methyl acetate phase, and a recycled aqueous acetic acid phase. A recycled phase may contain one or more of the foregoing components.

Distillation systems are employed that provide means for recovering the crude acetic acid and recycling catalyst solution, methyl iodide, methyl acetate, and other system components within the process. In a typical carbonylation process, carbon monoxide is continuously introduced into the carbonylation reactor, desirably below the agitator, which is used to stir the contents. The gaseous feed is thoroughly dispersed through the reacting liquid by this stirring means. A gaseous purge stream is desirably vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher, a catalyst-containing solution (catalyst phase) is withdrawn as a base stream (predominantly acetic acid containing the rhodium and the iodide salt along with lesser quantities of methyl acetate, methyl iodide, and water), while a vapor overhead stream comprising acetic acid is withdrawn overhead. The vapor overhead stream comprising acetic acid also contains methyl iodide, methyl acetate, and water. Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. The overhead stream is directed to the light ends column 14 as stream 26.

It has been disclosed in U.S. Pat. Nos. 6,143,930 and 6,339,171 that there is generally a higher concentration of the PRC's and in particular acetaldehyde content in the low-boiling overhead vapor stream 28 exiting column 14 than in the high-boiling residue stream exiting column 14. Thus, in accordance with the present invention, low-boiling overhead vapor stream 28 containing PRC's is subjected to additional processing to reduce and/or remove the amount of PRC's present. Low-boiling overhead vapor stream 28, therefore, is condensed and directed to an overhead receiver decanter 16. In addition to PRC's, low-boiling overhead vapor stream 28 will typically contain methyl iodide, methyl acetate, acetic acid, and water. Conditions are desirably maintained in the process such that low-boiling overhead vapor stream 28, once in decanter 16, will separate into a light phase and a heavy phase. Generally, low-boiling overhead vapor stream 28 is chilled to a temperature sufficient to condense and separate the condensable methyl iodide, methyl acetate, acetaldehyde and other carbonyl components, and water into two phases. A portion of stream 28 may include noncondensable gases such as carbon dioxide, hydrogen, and the like that can be vented as shown in stream 29 on FIG. 2.

The condensed light phase in decanter 16 will generally comprise water, acetic acid, and PRC's, as well as quantities of methyl iodide, methanol, and methyl acetate. The condensed heavy phase in decanter 16 will generally comprise methyl iodide, methyl acetate, and methanol. While either phase of the light ends overhead, i.e., low-boiling overhead vapor stream 28, may be subsequently processed to remove the PRC's and primarily the acetaldehyde component of the stream, the PRC's are preferably removed from the condensed light phase 30. Thus, the condensed heavy phase in the decanter 16 can be conveniently recirculated, either directly or indirectly, to the reactor (not shown in FIG. 2), and optionally recirculated with a portion of the light phase. For example, a portion of this condensed heavy phase can be recirculated to the reactor, with a slip stream, generally a small amount, e.g., 25 vol. %, preferably less than about 20 vol. %, of the heavy phase being directed to a carbonyl treatment process. This slip stream of the heavy phase may be treated individually or may be combined with the condensed light phase 30 for further distillation and extraction of carbonyl impurities.

In a preferred embodiment, the overall carbonylation process includes a step of distilling PRC's, primarily aldehydes such as acetaldehyde, from a low-boiling overhead vapor stream, particularly the condensed light phase of a low-boiling overhead vapor stream 28 from a light ends distillation column 14. In accordance with the present invention, a condensed light phase of a low-boiling overhead vapor stream 28 from a light ends distillation column 14 is distilled in one or more distillation columns and then subjected to single- or multi-stage extraction to reduce and/or remove PRC's. Preferably water derived from the hydrogenation system, described below, is employed as an extraction agent in at least one of the extraction stages.

Condensed light phase 30 is directed to one or more distillation columns 18 (one is shown), which serve to form a second vapor phase 36 enriched in PRC's, notably acetaldehyde, but also containing methyl iodide due to the similar boiling points of methyl iodide and acetaldehyde. Second vapor phase 36 is condensed and then extracted with water to reduce and/or remove PRC's, notably acetaldehyde. In a preferred embodiment a portion of the condensed stream 36 is provided as reflux to distillation column 18. This can be accomplished, as shown in FIG. 2, by provided the condensed stream 36 to an overhead receiver 20, from which a portion of condensed stream 36 can be provided to the extraction step (generally indicated as 70) by stream 40 and another portion of condensed stream 36 can be provided as reflux to distillation column 18 by stream 42.

Acetaldehyde is extracted by water to obtain an aqueous acetaldehyde stream 72, which may be treated as waste. The raffinate from the extraction, notably containing methyl iodide is desirably returned to the carbonylation process, e.g., to the reactor, the light ends column or the decanter 16, by stream 74. Aqueous acetaldehyde stream 72 optionally is stripped of aldehyde for treatment as waste with water being recirculated for use in the process.

A primary concern is in the extraction step that separates acetaldehyde from methyl iodide. The efficiency of this separation is primarily affected by the relative solubility of acetaldehyde and methyl iodide in water. While acetaldehyde is miscible in water, methyl iodide is not. However, the solubility of methyl iodide in water increases, with a concomitant loss of methyl iodide from the process system, with increasing levels of methyl acetate and/or methanol. At high enough methyl acetate and/or methanol levels, phase separation of methyl iodide in the water extraction may not occur. Similarly, phase separation of methyl iodide in the water extraction may not occur if acetic acid concentrations are sufficiently high. Thus, it is desirable that the distillate that is condensed and provided for extraction contain methanol and methyl acetate at a combined concentration of less than about 10 wt %, more desirably less than about 5 wt. %, even more desirably less than about 2 wt. %, and even more desirably less than about 1.5 wt. %. It is desirable that the distillate that is condensed and provided for extraction contains less than about 3 wt. % acetic acid, more desirably less than about 1 wt. %, and even more desirably less than about 0.5 wt. %. Particularly desired would be acetic acid concentrations approaching zero wt. %. The water purge streams from the hydrogenation process are well suited to be used as an extractant due to the relatively low concentrations of methyl acetate and/or methanol, as well as acetic acid.

Thus, in the process of the present invention, a single distillation is conducted in distillation column 18 under conditions designed to control, notably minimize, the quantities of methyl acetate and acetic acid in second vapor phase stream 36. Desirably, minimization of quantities of methyl acetate and acetic acid in second vapor phase stream 36 is achieved while simultaneously maintaining higher acetaldehyde levels in second vapor phase stream 36 than in the residuum of distillation column 18. It is desirable that the residuum of distillation column 18 contain less than about 0.3 wt. % acetaldehyde, more desirably less than about 0.2 wt. %, and even more desirably less than about 0.1 wt. %. Particularly desired would be acetaldehyde concentrations approaching zero wt. %.

Thus, in accordance with one embodiment of the present invention, illustrated in FIG. 2, low-boiling overhead vapor stream 28 is condensed in overhead receiver decanter 16 where it is biphasically separated to form a condensed heavy phase and a light condensed liquid phase 30. The light condensed liquid phase 30 is provided to distillation column 18 via stream 30/32. In this and other embodiments of the present invention, a portion of stream 30 can be directed back to the light ends column 14 as reflux stream 34.

In distillation column 18, a second vapor phase stream 36 overhead and a higher boiling liquid phase residuum stream 38 are formed. The second vapor phase stream 36 overhead is enriched with PRC's, notably acetaldehyde, with respect to the light condensed liquid phase 30. The second vapor phase stream 36 overhead is deficient with methyl acetate, methanol, and/or acetic acid (desirably all three) with respect to said light condensed liquid phase 30. The higher boiling liquid phase residuum stream 38 is enriched with methyl acetate, methanol, and/or acetic acid (desirably all three) with respect to said second vapor phase stream 36. Desirably, the second vapor phase stream 36 overhead is enriched with PRC's, notably acetaldehyde, with respect to the higher boiling liquid phase residuum stream 38. The higher boiling liquid phase residuum stream 38 can be, and preferably is, retained in the process.

One of ordinary skill in the art having the benefit of this disclosure can design and operate a distillation column to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

Further in accordance with this first embodiment of the present invention, second vapor phase stream 36 is extracted with water (generally indicated by 70), which is derived at least in part from the water stream formed in the hydrogenation system, as described below, to remove and/or reduce PRC's, notably acetaldehyde. Acetaldehyde is extracted by the water to obtain aqueous acetaldehyde stream 72, which is PRC-rich, and in particular acetaldehyde-rich. Aqueous acetaldehyde stream 72 will generally be treated as a waste, although in some embodiments acetaldehyde may be stripped, with the water optionally being recirculated to the process. The raffinate, notably containing methyl iodide is desirably returned to the carbonylation process by stream 74. The efficiency of the extraction will depend on such things as the number of extraction stages and the water to feed ratio.

Extraction with water 70 can be either a single stage or multistage extraction and any equipment used to conduct such extractions can be used in the practice of the present invention. Multistage extraction is preferred. For example, extraction 70 can be accomplished by combining stream 40 with water derived at least in part from the hydrogenation system and providing the combination successively to a mixer and then a separator. Multiple mixer/separator combinations can be operated in series to obtain a multistage extraction. Optionally, and desirably, multistage extraction is accomplished in a single vessel having a series of trays. The vessel may be equipped with paddle(s) or other mechanisms for agitation to increase extraction efficiency. In such a multistage extraction vessel, stream 40 is desirably provided proximate to one end of the vessel with water being provided proximate to the other end of the vessel or such other location to obtain a countercurrent flow.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 40 is exposed to minimize the likelihood of polymerization and condensation reactions involving acetaldehyde. Although it is preferred to use water from the hydrogenation system, water used in the extraction 70 may also be taken from an internal carbonylation stream so as to maintain water balance within the carbonylation system. Dimethyl ether (DME) may also be introduced to the extraction to improve the separation of methyl iodide in the extraction, i.e., to reduce the loss of methyl iodide into the aqueous acetaldehyde stream 72. The DME can be introduced to the process or formed in situ.

In accordance with another embodiment, also illustrated in FIG. 2, low-boiling overhead vapor stream 28 is condensed in decanter 16 where it is biphasically separated to form a condensed heavy phase and a condensed light phase 30. The condensed light phase 30 is provided to distillation column 18 via stream 30/32. Again, in this and other embodiments of the present invention, a portion of stream 30 can be directed back to the light ends column 14 as reflux stream 34. In distillation column 18, a second vapor phase stream 36 overhead and a higher boiling liquid phase residuum stream 38 are formed. A sidestream 80, comprising methyl acetate, is also taken. Thus, sidestream 80 may or may not be included in the PRS system.

If used, sidestream 80 allows the distillation column 18 to be operated under conditions desirable for obtaining a higher concentration of acetaldehyde in second vapor phase stream 36 while providing a mechanism for removing methyl acetate that might otherwise build up in the center of distillation column 18 or be pushed into the second vapor phase stream 36 overhead. The sidestream 80, comprising methyl acetate, is preferably retained in the process.

In embodiments employing sidestream 80, the second vapor phase stream 36 overhead is enriched with PRC, notably acetaldehyde, with respect to light condensed liquid phase 30. The second vapor phase stream 36 overhead is deficient with methyl acetate, methanol, and/or acetic acid (desirably all three) with respect to light condensed liquid phase 30. The second vapor phase stream 36 overhead is deficient with methyl acetate, methanol, and/or acetic acid (desirably all three) with respect to said sidestream 80 and, desirably, also with respect to the higher boiling liquid phase residuum stream 38. Desirably, the second vapor phase stream 36 overhead is enriched with PRC's, notably acetaldehyde, with respect to both the sidestream 80 and the higher boiling liquid phase residuum stream 38.

Further in accordance with this second embodiment of the present invention, second vapor phase stream 36 is extracted with water (generally indicated by 70) derived at least in part from the water stream formed in the hydrogenation system, as described below, to remove residual PRC's, notably acetaldehyde. When water is used as an extractant, it may be preferable to use a portion of the water of reaction in the hydrogenation process. Extraction in accordance with this second embodiment is conducted in accordance with the extraction procedures disclosed for the first embodiment.

Operating without a sidestream 80, the process has been found to achieve the following results respecting the separation capabilities of distillation column 18, as shown in Table 1.

TABLE 1

EXEMPLARY STREAM COMPOSITIONS WITHOUT SIDESTREAM 80

| Component | Weight Percent in Stream 30/32 | Weight Percent in Stream 36 | Weight Percent in Stream 38 |
| --- | --- | --- | --- |
| Methyl iodide | 1.5 | 74.5 | <0.1 |
| Methyl acetate | 6.0 | 1.4 | 6.1 |
| Methanol | 4.0 | 0.2 | 4.1 |
| Acetic acid | 15 | <0.1 | 15.3 |
| Water | 73 | 1.6 | 74.5 |
| Acetaldehyde | 0.5 | 22.2 | 0.1 |

Operating with a sidestream 80, it is expected that the following results respecting the separation capabilities of distillation column 18 can be achieved, as shown in Table 2.

TABLE 2

EXEMPLARY STREAM COMPOSITIONS WITH SIDESTREAM 80

| Component | Weight Percent in Stream 30/32 | Weight Percent in Stream 36 | Weight Percent in Stream 38 | Weight Percent in Stream 80 |
| --- | --- | --- | --- | --- |
| Methyl iodide | 1.5 | 46.8 | <0.1 | 28.7 |
| Methyl acetate | 4.0 | 0.4 | 1.7 | 60.4 |
| Methanol | 1.0 | <0.1 | 1.0 | 0.5 |
| Acetic acid | 15 | <0.1 | 15.7 | 0.5 |
| Water | 78 | 0.8 | 81.6 | 7.4 |
| Acetaldehyde | 0.5 | 52 | <0.1 | 2.5 |

This process has been found to reduce and/or remove PRC's and their precursors, multi-carbon alkyl iodide impurities, and propionic and higher carboxylic acids from the carbonylation process. It has also been shown that acetaldehyde and its derivatives are reduced and/or removed by sufficient amounts such that it is possible to keep the concentration of propionic acid in the acetic acid product below about 500 parts per million by weight, preferably below about 300 parts per million, and most preferably below 250 parts per million.

In variations of the embodiments of the present invention, it is important to inhibit the formation of various aldehyde related polymers and condensation products in distillation column 18. Acetaldehyde polymerizes to form metaldehyde and paraldehyde. These polymers generally are low molecular weight, less than about 200. Higher molecular weight polymers of acetaldehyde can also form. These higher molecular weight polymers (molecular weight greater than about 1000) are believed to form during processing of the light phase and are viscous and thixotropic. Acetaldehyde can also undergo undesirable aldol condensation reactions.

The formation of these impurities, i.e., metaldehyde and paraldehyde and higher molecular weight polymers of acetaldehyde, can be suppressed by introducing into distillation column 18 a flush stream containing at least water and/or acetic acid.

Hydrogenation System

As discussed above, the processes of the invention integrate a carbonylation system with a hydrogenation system. The hydrogenation system preferably includes a hydrogenation reactor and a hydrogenation catalyst system effective in converting acetic acid to ethanol and water. The hydrogenation system also includes a separation system for separating a crude ethanol product into an ethanol product stream, a water stream (which is directed at least in part to the carbonylation system, e.g., an extraction unit in said carbonylation system), and optionally one or more byproduct streams.

In addition to acetic acid, the acetic acid feed stream that is fed to the hydrogenation reactor may comprise other carboxylic acids and anhydrides, as well as aldehydes and/or ketones, such as acetaldehyde and acetone. Preferably, a suitable acetic acid feed stream comprises one or more compounds selected from the group consisting of acetic acid, acetic anhydride, acetaldehyde, ethyl acetate, and mixtures thereof. These compounds may also be hydrogenated in the processes of the present invention. In some embodiments, the presence of some carboxylic acids, such as propanoic acid or its anhydride, may be beneficial in producing propanol. Water may also be present in the acetic acid feed.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of: sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain N or Pro. The Saint-Gobain N or Pro SS61138 silica exhibits the following properties: contains approximately 95 wt. % high surface area silica; surface area of about 250 $m^2$/g; median pore diameter of about 12 nm; average pore volume of about 1.0 $cm^3$/g as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a mole percentage based on acetic acid in the feed. For example, acetic acid may have a conversion that is greater than 40%, e.g., greater than 50%, greater than 70% or greater than 90%. The conversion may vary and may be from 40% to 70% in some embodiments and from 85% to 99% in others.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, in the reactor, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol mixture produced by the reactor, before any subsequent processing, such as purification and separation, will typically comprise acetic acid, ethanol and water. Exemplary compositional ranges for the crude ethanol mixture are provided in Table 3. The "others" identified in Table 3 may include, for example, esters, ethers, aldehydes, ketones, alkanes, and carbon dioxide.

TABLE 3

CRUDE ETHANOL MIXTURE COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 5 to 70 | 5 to 50 |
| Water | 5 to 35 | 5 to 28 | 10 to 26 | 10 to 22 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Diethyl Acetal | 0.001 to 5 | 0.01 to 3 | 0.1 to 2 | 0.5 to 1.5 |
| Others | 0.1 to 10 | 0.1 to 6 | 0.1 to 4 | — |

In one embodiment, the crude ethanol mixture may comprise acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Figure 3:
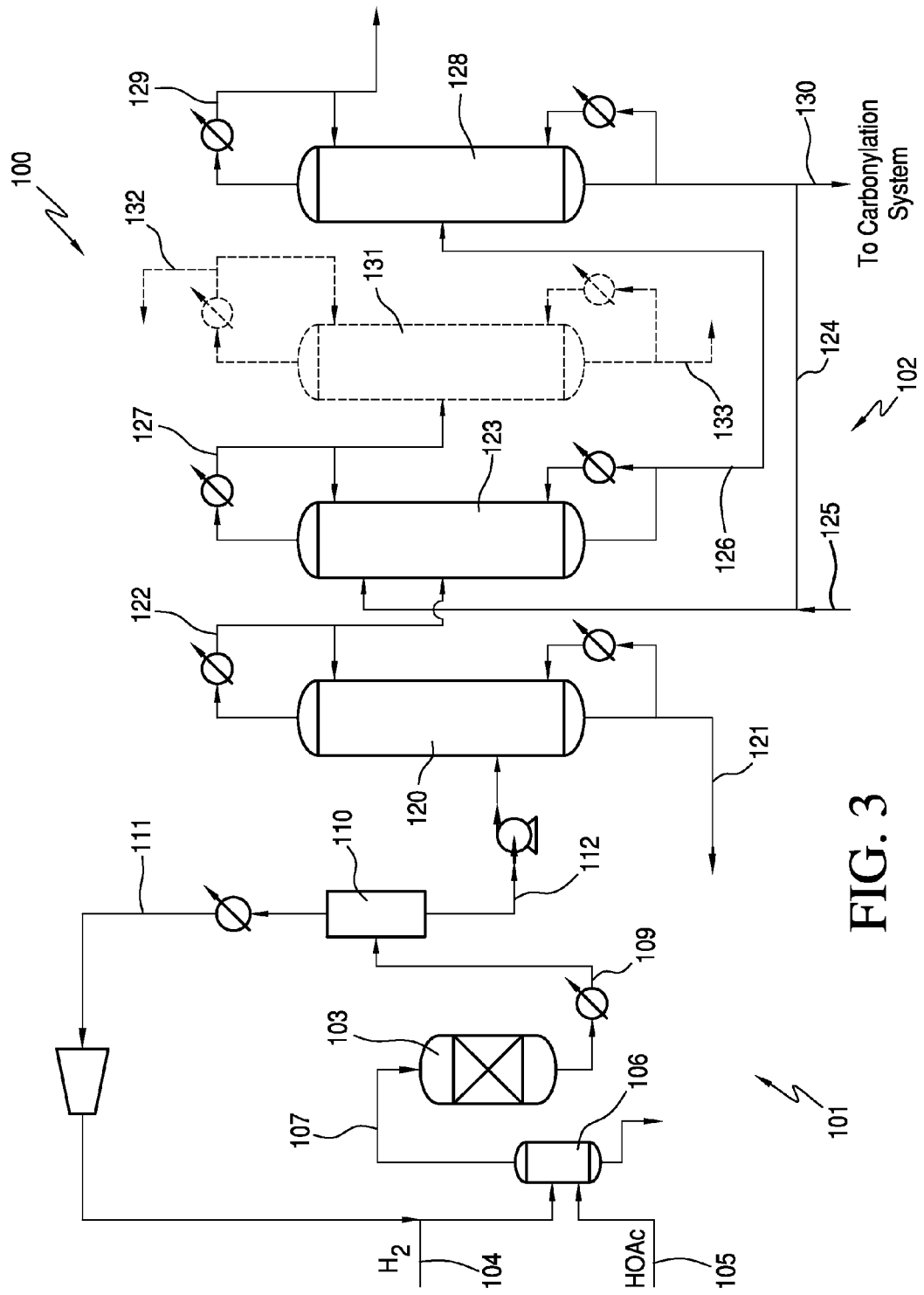
FIG. 3 is a schematic diagram of a hydrogenation process having four columns in accordance with an embodiment of the present invention.
Figure 4:
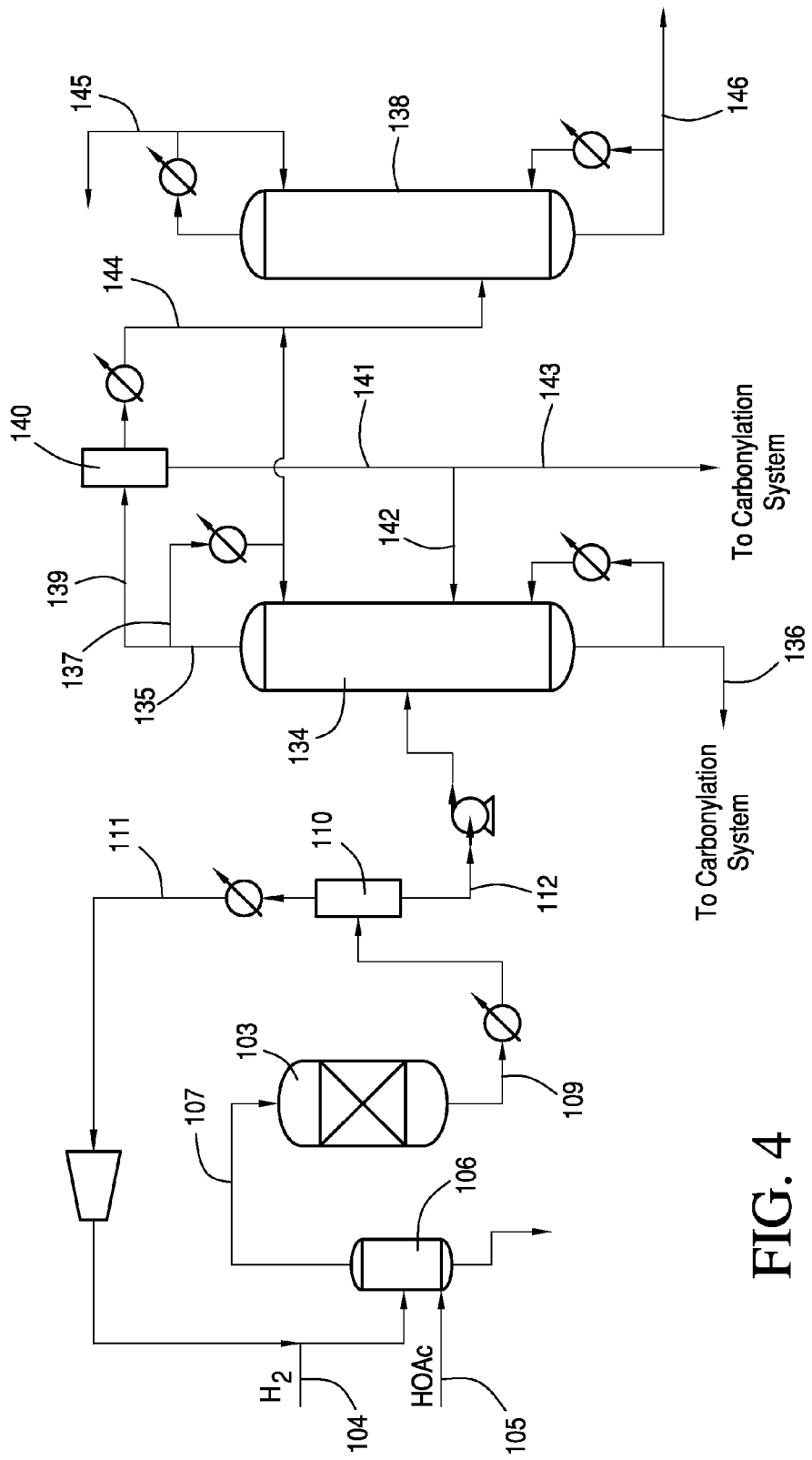
FIG. 4 is a schematic diagram of another hydrogenation process having two columns with an intervening water separation in accordance with an embodiment of the present invention.
Figure 5:
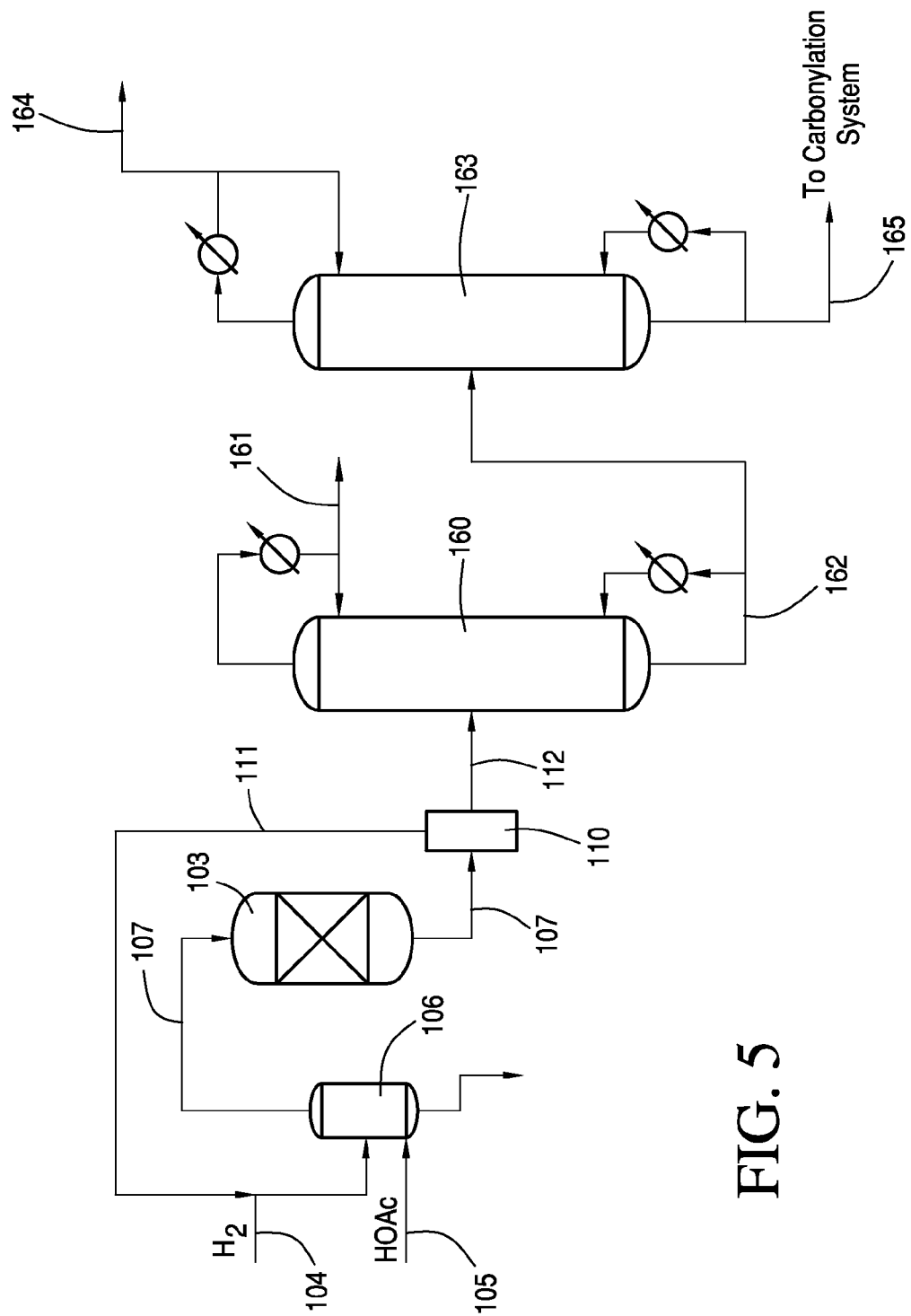
FIG. 5 is a schematic diagram of another hydrogenation process having two columns in accordance with an embodiment of the present invention.

Ethanol may be recovered using several different techniques. In FIG. 3, hydrogenation section separates the crude ethanol mixture using three columns 120, 123, 128 and/or an optional fourth column 131. In FIG. 4, the crude ethanol mixture is separated in two columns with an intervening water separation step. In FIG. 5, the separation of the crude ethanol mixture uses two columns. Other separation systems may also be used with embodiments of the present invention. For purposes of convenience, the columns in each exemplary separation process may be referred to as the first column, second column, third column, etc., but it should be understood that similarly named columns of the embodiments shown in FIGS. 3-5 will operate differently from one another.

In each of the figures, hydrogenation system 100 includes a reaction zone 101 and a separation zone 102. Hydrogen and acetic acid are fed via lines 104 and 105, respectively, to a vaporizer 106 to create a vapor feed stream in line 107 that is directed to reactor 103. In one embodiment, lines 104 and 105 may be combined and jointly fed to vaporizer 106. The temperature of the vapor feed stream in line 107 is preferably from 100° C. to 350° C., e.g., from 120° C. to 310° C. or from 150° C. to 300° C. Any feed that is not vaporized is removed from vaporizer 106 and may be recycled thereto or discarded. In addition, although line 107 is shown as being directed to the top of reactor 103, line 107 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol mixture stream is withdrawn, preferably continuously, from reactor 103 via line 109.

The crude ethanol mixture stream in line 109 may be condensed and fed to a separator 110, which, in turn, provides a vapor stream 111 and a liquid stream 112. In some embodiments, separator 110 may comprise a flasher or a knockout pot. The separator 110 may operate at a temperature of from 20° C. to 250° C., e.g., from 30° C. to 225° C. or from 60° C. to 200° C. The pressure of separator 110 may be from 50 kPa to 2000 kPa, e.g., from 75 kPa to 1500 kPa or from 100 kPa to 1000 kPa. Optionally, the crude ethanol mixture in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to reaction zone 101, vapor stream 110 may be combined with the hydrogen feed 104 and co-fed to vaporizer 106. In some embodiments, the returned vapor stream 111 may be compressed before being combined with hydrogen feed 104.

In FIG. 3, the liquid stream 112 from separator 110 is withdrawn and pumped to the side of first column 120, also referred to as an "acid separation column." In one embodiment, the contents of liquid stream 112 are substantially similar to the crude ethanol mixture obtained from the reactor, except that the composition has been depleted of hydrogen, carbon dioxide, methane and/or ethane, which are removed by separator 110. Accordingly, liquid stream 112 may also be referred to as a crude ethanol mixture. Exemplary components of liquid stream 112 are provided in Table 4. It should be understood that liquid stream 112 may contain other components, not listed in Table 4.

TABLE 4

COLUMN FEED COMPOSITION (Liquid Stream 112)

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 5 to 70 |
| Water | 5 to 35 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 4 may include, but are not limited to, ethyl propionate, methyl acetate, isopropyl acetate, n-propyl acetate, n-butyl acetate or mixtures thereof. The "other ethers" in Table 4 may include, but are not limited to, diethyl ether, methyl ethyl ether, isobutyl ethyl ether or mixtures thereof. The "other alcohols" in Table 4 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol mixture in line 109 or in liquid stream 112 may be further fed to an esterification reactor, hydrogenolysis reactor, or combination thereof. An esterification reactor may be used to consume residual acetic acid present in the crude ethanol mixture to further reduce the amount of acetic acid that would otherwise need to be removed. Hydrogenolysis may be used to convert ethyl acetate in the crude ethanol mixture to ethanol.

In the embodiment shown in FIG. 3, line 112 is introduced in the lower part of first column 120, e.g., lower half or lower third. In first column 120, acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 106 may reduce the amount of heavies that need to be purged from vaporizer 106. Reducing the amount of heavies to be purged may improve efficiencies of the process while reducing byproducts.

First column 120 also forms an overhead distillate, which is withdrawn in line 122, and which may be condensed and refluxed, for example, at a ratio of from 10:1 to 1:10, e.g., from 3:1 to 1:3 or from 1:2 to 2:1. The distillate in line 122 comprises primarily ethanol, as well as water, ethyl acetate, acetaldehyde, and/or diethyl acetal. For example, distillate may comprise from 20 to 75 wt. % ethanol and 10 to 40 wt. % ethanol. Preferably, the concentration of acetic acid in the distillate is less than 2 wt. %, e.g., less than 1 wt. % or less than 0.5 wt. %.

In one embodiment, first column 120 may be operated at ambient pressure. In other embodiments, the pressure of first column 120 may range from 0.1 kPa to 510 kPa, e.g., from 1 kPa to 475 kPa or from 1 kPa to 375 kPa. When first column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C.

As shown, the first distillate in line 122 is introduced to the second column 123, also referred to as the "light ends column," preferably in the middle part of column 123. Preferably the second column 123 is an extractive distillation column, and an extraction agent is added thereto via lines 124 and/or 125. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 122 that is fed to the second column 123 comprises ethanol, water, and ethyl acetate. These compounds tend to form binary and ternary azeotropes, which decrease separation efficiency. As shown, in one embodiment the extraction agent comprises the third residue in line 124. Preferably, the recycled third residue in line 124 is fed to second column 123 at a point higher than the first distillate in line 122. In one embodiment, the recycled third residue in line 124 is fed near the top of second column 123 or fed, for example, above the feed in line 122 and below the reflux line from the condensed overheads. In a tray column, the third residue in line 124 is continuously added near the top of the second column 123 so that an appreciable amount of the third residue is present in the liquid phase on all of the trays below. In another embodiment, the extraction agent is fed from a source outside of the process 100 via line 125 to second column 123. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 120 trays, e.g., from 15 to 80 trays or from 20 to 70 trays. The temperature of second column 123 at atmospheric pressure may vary. Second column 123 may operate at a pressure ranging from 0.1 kPa to 510 kPa, e.g., from 1 kPa to 475 kPa or from 1 kPa to 375 kPa. In one embodiment second residue exiting in line 126 preferably is at a temperature from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C.

The second residue in line 126 comprises ethanol and water. The second residue may comprise less than 3 wt. % ethyl acetate, e.g., less than 1 wt. % ethyl acetate or less than 0.5 wt. % ethyl acetate. The second distillate in line 127 comprises ethyl acetate, acetaldehyde, and/or diethyl acetal. In addition, minor amounts of ethanol may be present in the second distillate. The weight ratio of ethanol in the second residue to second distillate preferably is at least 3:1, e.g., at least 6:1, at least 8:1, at least 10:1 or at least 15:1.

All or a portion of the third residue is recycled to the second column. In one embodiment, all of the third residue may be recycled until process 100 reaches a steady state at which point a portion of the third residue may be recycled with the remaining portion being purged from the system 100. The composition of the second residue will tend to have lower amounts of ethanol than when the third residue is not recycled. As the third residue is recycled, the composition of the second residue comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 3, for example, at a reflux ratio of from 1:10 to 10:1, e.g., from 1:3 to 3:1 or from 1:2 to 2:1. The third residue in line 124, which comprises primarily water, preferably is returned to the second column 123 as an extraction agent as described above. In one embodiment, a first portion of the third residue in line 124 is recycled to the second column and a second portion is purged and removed from the system via line 130. In one embodiment, once the process reaches steady state, the second portion of water to be purged is substantially similar to the amount of water formed in the hydrogenation of acetic acid. In one embodiment, a portion of the third residue may be used to hydrolyze any other stream, such as one or more streams comprising ethyl acetate. In one embodiment, the third residue in line 124 is withdrawn from third column 128 at a temperature higher than the operating temperature of the second column 123. Preferably, the third residue in line 124 is integrated to heat one or more other streams or is reboiled prior to be returned to the second column 123.

Although FIG. 3 show the third residue being directly recycled to second column 123, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 128 is preferably a tray column. In one embodiment, third column 128 may operate at a pressure from 0.1 kPa to 510 kPa, e.g., from 1 kPa to 475 kPa or from 1 kPa to 375 kPa. At atmospheric pressure, the temperature of the third distillate exiting in line 129 preferably is from 60° C. to 110° C., e.g., from 70° C. to 100° C. or from 75° C. to 95° C. The temperature of the third residue in line 124 preferably is from 70° C. to 115° C., e.g., from 80° C. to 110° C. or from 85° C. to 105° C.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100. The composition of the ethanol product obtained from the third distillate in FIG. 3 is shown below in Table 5.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 3, at a reflux ratio of 1:10 to 10:1, e.g., from 1:5 to 5:1 or from 1:3 to 3:1. The second distillate in line 127 may be purged or recycled to the reaction zone. The second distillate in line 127 may be further processed in an optional fourth column 131, also referred to as the "acetaldehyde removal column." In optional fourth column 131, the second distillate is separated into a fourth distillate, which comprises acetaldehyde, in line 132 and a fourth residue, which comprises ethyl acetate, in line 133. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101. For example, the fourth distillate may be combined with the acetic acid feed, added to the vaporizer 106, or added directly to the reactor 103. The fourth distillate preferably is co-fed with the acetic acid in feed line 105 to vaporizer 106. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of optional fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Optional fourth column 131 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C.

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate, e.g. intermediate stream, in line 129 may have lower concentrations of aldehydes and esters due to the recycling of third residue in line 124.

Although the composition of the third residue may vary depending on the specific separation conditions, in preferred embodiments the third residue comprises water and may be referred to herein as a water stream. Due to the presence of acetic acid in the water stream the pH may range from 2.99 to 3.35. In one embodiment, the water stream may be substantially free of organic impurities, except for acetic acid. Exemplary compositions for the third distillate and third residue (water stream) are provided below in Table 5. It should also be understood that the distillate may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue (Water Stream) |  |  |  |
| Water | 97 to 100 | 98 to 100 | 99 to 100 |
| Ethanol | <0.005 | <0.002 | <0.001 |
| Ethyl Acetate | <0.001 | <0.0005 | not detectable |
| Acetic Acid | <0.5 | <0.1 | <0.05 |
| Organic Impurities | <0.001 | <0.0005 | not detectable |

As shown in FIG. 3, all or a portion of the third residue stream is directed to the carbonylation system, e.g., as shown in FIG. 2, to serve as an extraction medium. In a preferred embodiment, all or a portion of the third residue is directed to the PRS of the carbonylation system to serve as an extractant (e.g., stream 70 in FIG. 2) for extracting acetaldehyde from a mixture comprising methyl iodide and acetaldehyde.

FIG. 4 illustrates another exemplary separation system that has a similar reaction zone 101 as FIG. 3 and produces a liquid stream 112, e.g., crude ethanol mixture, for further separation. In one preferred embodiment, the reaction zone 101 of FIG. 4 operates at above 70% acetic acid conversion, e.g., above 85% conversion or above 90% conversion. Thus, the acetic acid concentration in the liquid stream 112 may be low.

Liquid stream 112 is fed to the first column 134 to yield a first distillate 135 and first residue 136. Liquid stream 112 may be introduced in the middle or lower portion of first column 134, also referred to as acid-water column. In one embodiment, no entrainers are added to first column 134. Water and acetic acid, along with any other heavy components, if present, are removed from liquid stream 112 and are withdrawn, preferably continuously, as a first residue in line 136. Preferably, a substantial portion of the water in the crude ethanol mixture that is fed to first column 134 may be removed in the first residue, for example, up to about 75% or to about 90% of the water from the crude ethanol mixture. In one embodiment, 30 to 90% of the water in the crude ethanol mixture is removed in the residue, e.g., from 40 to 88% of the water or from 50 to 84% of the water.

When first column 134 is operated under about 170 kPa, the temperature of the residue exiting in line 136 preferably is from 90° C. to 130° C., e.g., from 95° C. to 120° C. or from 100° C. to 115° C. The temperature of the distillate exiting in line 135 preferably is from 60° C. to 90° C., e.g., from 65° C. to 85° C. or from 70° C. to 80° C. In some embodiments, the pressure of first column 134 may also range from 0.1 kPa to 510 kPa, e.g., from 1 kPa to 475 kPa or from 1 kPa to 375 kPa.

The first distillate in line 135 comprises some water in addition to ethanol and other organics. In terms of ranges, the water concentration in the first distillate in line 135 preferably is from 4 wt. % to 38 wt. %, e.g., from 7 wt. % to 32 wt. %, or from 7 to 25 wt. %. A portion of first distillate in line 137 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 134. The condensed portion of the first distillate may also be fed to a second column 138.

As shown, the remaining portion of the first distillate in line 139 is fed to a water separation unit 140. Water separation unit 140 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 140 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise from two to five beds. Water separator 140 may remove at least 95% of the water from the portion of first distillate in line 139, and more preferably from 99% to 99.99% of the water from the first distillate, in a water stream 141. All or a portion of water stream 141 may be returned to first column 134 in line 142, where the water preferably is ultimately recovered from column 134 in the first residue in line 136. Additionally or alternatively, all or a portion of water stream 141 may be removed from the hydrogenation system via line 143. The remaining portion of first distillate exits the water separator 140 as ethanol mixture stream 144. Ethanol mixture stream 144 may have a low water concentration of less than 10 wt. %, e.g., less than 6 wt. % or less than 2 wt. %.

In this aspect of the invention, either or both the first residue in line 136 and/or the separated stream in line 143 comprise water and may be referred to as a water stream. Exemplary compositions for line 136 and line 143 are provided in Table 6, below. It should also be understood that these streams may also contain other components, not listed, such as components derived from the feed.

TABLE 6

WATER STREAMS IN FIG. 4

|  | Conc. (wt. %) | Conc. (wt. %) | Conc. (wt. %) |
|---|---|---|---|
| First Residue 136 |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |
| Water Stream 143 |  |  |  |
| Water | 80 to 100 | 85 to 99.5 | 90 to 99 |
| Ethanol | <10 | 0.001 to 5 | 0.01 to 0.5 |
| Ethyl Acetate | <10 | 0.001 to 5 | 0.01 to 0.5 |

In one embodiment, all or a portion of either or both the first residue in line 136 and/or the separated stream in line 143 may be directed to the carbonylation system, e.g., as shown in FIG. 2, to serve as an extraction medium. In a preferred embodiment, all or a portion of the first residue and/or line 143 is directed to the PRS of the carbonylation system to serve as an extractant (e.g., stream 70 in FIG. 2) for extracting acetaldehyde from a mixture comprising methyl iodide and acetaldehyde.

Preferably, ethanol mixture stream 144 is not returned or refluxed to first column 135. The condensed portion of the first distillate in line 137 may be combined with ethanol mixture stream 144 to control the water concentration fed to the second column 138. For example, in some embodiments the first distillate may be split into equal portions, while in other embodiments, all of the first distillate may be condensed or all of the first distillate may be processed in the water separation unit. In FIG. 4, the condensed portion in line 137 and ethanol mixture stream 144 are co-fed to second column 138. In other embodiments, the condensed portion in line 137 and ethanol mixture stream 144 may be separately fed to second column 138. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 138 in FIG. 4, also referred to as the "light ends column," removes ethyl acetate and acetaldehyde from the first distillate in line 137 and/or ethanol mixture stream 144. Ethyl acetate and acetaldehyde are removed as a second distillate in line 145 and ethanol is removed as the second residue in line 146. Preferably ethanol is recovered with low amounts of ethyl acetate, acetaldehyde, and/or acetal, e.g., less than 1 wt. % or more preferably less than 0.5 wt. %. The ethanol product obtained from second residue in FIG. 4, is shown below in Table 8. Preferably, the ethanol product comprises less than 1 wt. % diethyl acetal, e.g., less than 0.5 wt. % or less than 0.01 wt. %.

Second column 138 may be a tray column or packed column. In one embodiment, second column 138 is a tray column having from 5 to 120 trays, e.g., from 15 to 100 trays or from 20 to 90 trays. In one embodiment, second column 138 operates at a pressure from 101 kPa to 5,000 kPa, e.g., from 120 kPa to 4,000 kPa, or from 150 kPa to 3,000 kPa. In other embodiments, second column 138 may operate at a pressure ranging from 0.1 kPa to 510 kPa, e.g., from 10 kPa to 450 kPa or from 50 kPa to 350 kPa. Although the temperature of second column 138 may vary, when at about 20 kPa to 70 kPa, the temperature of the second residue exiting in line 146 preferably is from 30° C. to 75° C., e.g., from 35° C. to 70° C. or from 40° C. to 65° C. The temperature of the second distillate exiting in line 145 preferably is from 20° C. to 55° C., e.g., from 25° C. to 50° C. or from 30° C. to 45° C.

The total concentration of water fed to second column 138 preferably is less than 10 wt. %, as discussed above. When first distillate in line 137 and/or ethanol mixture stream 144 comprises minor amounts of water, e.g., less than 1 wt. % or less than 0.5 wt. %, additional water may be fed to the second column 138 as an extractive agent in the upper portion of the column. A sufficient amount of water is preferably added via the extractive agent such that the total concentration of water fed to second column 138 is from 1 to 10 wt. % water, e.g., from 2 to 6 wt. %, based on the total weight of all components fed to second column 138. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

The second distillate in line 145, which comprises ethyl acetate and/or acetaldehyde, preferably is refluxed as shown in FIG. 4, for example, at a reflux ratio of from 1:30 to 30:1, e.g., from 1:10 to 10:1 or from 1:3 to 3:1. In one aspect, not shown, the second distillate 145 or a portion thereof may be returned to reactor 103.

In one embodiment, the second distillate in line 145 and/or a refined second distillate, or a portion of either or both streams, may be further separated to produce an acetaldehyde-containing stream and an ethyl acetate-containing stream. For example, the optional fourth column 131 of FIG. 3 may be used to separate second distillate in line 145. This may allow a portion of either the resulting acetaldehyde-containing stream or ethyl acetate-containing stream to be recycled to reactor 103 while purging the other stream. The purge stream may be valuable as a source of either ethyl acetate and/or acetaldehyde. In one embodiment, it may be preferred to operate second column 138 in FIG. 4 at a pressure less than atmospheric pressure to decrease the energy required to separate ethyl acetate and ethanol.

Another exemplary two column separation scheme is shown in FIG. 5. In this embodiment, liquid stream 112 is introduced in the upper part of first column 160, e.g., upper half or upper third. In one embodiment, no entrainers are added to first column 160. In first column 160, a weight majority of the ethanol, water, acetic acid, and other heavy components, if present, are removed from liquid stream 112 and are withdrawn, preferably continuously, as the first residue in line 162. First column 160 also forms an overhead distillate, which is withdrawn in line 161, and which may be condensed and refluxed, for example, at a ratio of from 30:1 to 1:30, e.g., from 10:1 to 1:10 or from 1:5 to 5:1. The first distillate in line 161 preferably comprises a weight majority of the ethyl acetate from liquid line 112. In addition, distillate in line 161 may also comprise acetaldehyde.

When column 160 is operated under about 170 kPa, the temperature of the residue exiting in line 162 preferably is from 70° C. to 155° C., e.g., from 90° C. to 130° C. or from 100° C. to 110° C. The base of column 160 may be maintained at a relatively low temperature by withdrawing a residue stream comprising ethanol, water, and acetic acid, thereby providing an energy efficiency advantage. The temperature, at 170 kPa, of the distillate exiting in line 161 preferably is from 75° C. to 100° C., e.g., from 75° C. to 83° C. or from 81° C. to 84° C.

In one embodiment, column 160 of FIG. 5 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 162 to water in the distillate in line 161 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 ppm, less than 500 ppm or less than 100 ppm acetic acid. The distillate may be purged from the system or recycled in whole or part to reactor 103. In some embodiments, the distillate may be further separated, e.g., in an optional fourth column of FIG. 3, into an acetaldehyde stream and an ethyl acetate stream. Either of these streams may be returned to the reactor 103 or separated from system 100 as a separate product.

To recover ethanol, the residue in line 162 may be further separated in a second column 163, also referred to as an "acid separation column." An acid separation column may be used when the acetic acid concentration in the first residue is greater than 1 wt. %, e.g., greater than 5 wt. %. The first residue in line 162 is introduced to second column 163 preferably in the top part of column 163, e.g., top half or top third. Second column 163 yields a second residue in line 165 comprising acetic acid and water, and a second distillate in line 164 comprising ethanol.

Second column 163 may be a tray column or packed column. In one embodiment, second column 163 is a tray column having from 5 to 150 trays, e.g., from 15 to 50 trays or from 20 to 45 trays. In some embodiments, the second column 163 of FIG. 5 is operated at a pressure ranging from 0.1 kPa to 510 kPa, e.g., from 1 kPa to 475 kPa or from 1 kPa to 375 kPa. In the system shown in FIG. 5, it is preferred to operate the first column 160 at an increased pressure, because second column 163 comprises very low amounts of acetaldehyde and/or acetals. At atmospheric pressure the temperature of the second residue exiting in line 165 preferably is from 95° C. to 130° C., e.g., from 100° C. to 125° C. or from 110° C. to 120° C. The temperature of the second distillate exiting in line 164 preferably is from 60° C. to 105° C., e.g., from 75° C. to 100° C. or from 80° C. to 100° C.

The weight ratio of ethanol in the second distillate in line 164 to ethanol in the second residue in line 165 preferably is at least 35:1. In one embodiment, the weight ratio of water in the second residue 165 to water in the second distillate 164 is greater than 2:1, e.g., greater than 4:1 or greater than 6:1. In addition, the weight ratio of acetic acid in the second residue 165 to acetic acid in the second distillate 164 preferably is greater than 10:1, e.g., greater than 15:1 or greater than 20:1. Preferably, the second distillate in line 164 is substantially free of acetic acid and may only contain, if any, trace amounts of acetic acid. Preferably, the second distillate in line 164 contains substantially no ethyl acetate.

The remaining water from the second distillate in line 164 may be removed in further embodiments of the present invention. Depending on the water concentration, the ethanol product may be derived from the second distillate in line 164. Some applications, such as industrial ethanol applications, may tolerate water in the ethanol product, while other applications, such as fuel applications, may require an anhydrous ethanol. The amount of water in the distillate of line 164 may be closer to the azeotropic amount of water, e.g., at least 4 wt. %, preferably less than 20 wt. %, e.g., less than 12 wt. % or less than 7.5 wt. %. Water may be removed from the second distillate in line 164 using several different separation techniques as described herein. Particularly preferred techniques include the use of distillation column, membranes, adsorption units, and combinations thereof.

In one embodiment of the invention, the second residue 165 comprises primarily water and may be referred to as a water stream. Exemplary compositions for second residue 165 are provided in Table 7, below.

TABLE 7

EXEMPLARY COMPOSITIONS FOR WATER STREAM 165 IN FIG. 5

| | Conc. (wt. %) | Conc. (wt. %) | Conc. (wt. %) |
|---|---|---|---|
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

In one embodiment, all or a portion of the second residue 165 is directed to a carbonylation system, e.g., as shown in FIG. 2, to serve as an extraction medium. In a preferred embodiment, all or a portion of the second residue 165 is directed to the PRS of the carbonylation system to serve as an extractant (e.g., stream 70 in FIG. 2) for extracting acetaldehyde from a mixture comprising methyl iodide and acetaldehyde.

In one embodiment, any of the residue streams from FIGS. 3-5 may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 103. The resulting water stream may be directed to a carbonylation system for use as an extractant as discussed above.

In other embodiments, for example, where the second residue comprises less than 50 wt. % acetic acid, possible options include one or more of: (i) neutralizing the acetic acid, or (ii) reacting the acetic acid with an alcohol. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

The columns shown in figures may comprise any distillation column capable of performing the desired separation and/or purification. For example, other than the acid columns describe above, the other columns preferably are a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from exemplary systems shown in the figures. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 8.

TABLE 8

FINISHED ETHANOL COMPOSITIONS

| Component | Conc. (wt. %) | Conc. (wt. %) | Conc. (wt. %) |
| --- | --- | --- | --- |
| Ethanol | 75 to 99.9 | 80 to 99.5 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Diethyl Acetal | <1 | 0.0001 to 0.1 | 0.0001 to 0.01 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 8, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
   carbonylating methanol in a carbonylation system in the presence of a carbonylation catalyst under conditions effective to form acetic acid;
   hydrogenating the acetic acid in a hydrogenation system in the presence of a hydrogenation catalyst to form a crude ethanol product comprising ethanol and water;
   separating the ethanol from the water to form an ethanol stream and a water stream; and
   using at least a portion of the water stream as an extractant in the carbonylation system.

2. The process of claim 1, wherein the carbonylation process forms a PRC stream comprising one or more PRC's and methyl iodide, the process further comprising the step of:
   adding at least a portion of the water stream to the PRC stream to form an aqueous phase comprising the separated water and a majority of the one or more PRC's, and an organic phase comprising a majority of the methyl iodide.

3. The process of claim 1, wherein the water stream contains less than 0.3 wt. % of organic impurities other than acetic acid.

4. The process of claim 1, wherein the crude ethanol product comprises ethanol, water, and ethyl acetate.

5. The process of claim 4, wherein the crude ethanol product comprises ethanol in an amount of from 5 to 70 wt. %, water in an amount of from 5 to 35 wt. %, and ethyl acetate in an amount of from 0 to 20 wt. %.

6. The process of claim 1, wherein the water stream comprises:
   at least 97 wt. % water;
   less than 0.5 wt. % acetic acid;
   less than 0.005 wt. % ethanol; and
   less than 0.001 wt. % ethyl acetate.

7. The process of claim 1, wherein the water stream has a pH ranging from 2.99 to 3.35.

8. The process of claim 1, wherein the separating comprises:
   separating at least a portion of the crude ethanol product in a first column into a first distillate comprising ethanol, water and ethyl acetate, and a first residue comprising water;
   separating at least a portion of the first distillate in a second column into a second distillate comprising ethyl acetate and a second residue comprising ethanol and water; and
   separating at least a portion of the second residue in a third column into a third distillate comprising ethanol and a third residue comprising the water stream.

9. The process of claim 8, wherein the second column is an extractive distillation column, which utilizes an extraction agent.

10. The process of claim 9, wherein at least a portion of the water stream is directed to the second column.

11. The process of claim 1, wherein the hydrogenation catalyst comprises a combination of metals selected from the group consisting of platinum/ruthenium, platinum/rhenium, palladium/ruthenium, palladium/rhenium, platinum/tin, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

12. The process of claim 1, wherein the separating comprises:
   separating at least a portion of the crude ethanol product in a first column into a first distillate comprising ethyl acetate, acetaldehyde and ethanol, and a first residue comprising water and acetic acid, wherein the water stream that is used as the extractant in the carbonylation system is an aliquot or non-aliquot portion of the first residue.

13. The process of claim 1, wherein the separating comprises:
   separating at least a portion of the crude ethanol product in a first column into a first distillate comprising ethyl acetate, acetaldehyde and ethanol, and a first residue comprising water and acetic acid, wherein at least a portion of the water stream that is used as the extractant in the carbonylation system is derived from the first residue.

14. The process of claim 13, wherein the first distillate further comprises water and the process further comprises the step of removing additional water from the first distillate, wherein at least a portion of the water stream that is used as the extractant in the carbonylation system is derived from the additional water.

15. A process for producing a water stream, the process comprising:
   providing a crude ethanol product comprising ethanol, water, ethyl acetate, and acetic acid;
   separating at least a portion of the crude ethanol product into an ethanol stream and a water stream, wherein the water stream contains less than 0.3 wt. % of organic impurities other than acetic acid; and
   using at least a portion of the water stream as an extractant in a carbonylation system.

16. The process of claim 15, wherein the carbonylation process forms a PRC stream comprising one or more PRC's and methyl iodide, the process further comprising the step of:
   adding at least a portion of the water stream to the PRC stream to form an aqueous phase comprising the separated water and a majority of the one or more PRC's, and an organic phase comprising a majority of the methyl iodide.

17. An integrated process for producing ethanol, the process comprising the steps of:
   carbonylating methanol in a carbonylation system in the presence of a carbonylation catalyst under conditions effective to form a crude acetic acid product comprising acetic acid, one or more PRC's, and methyl iodide;
   separating the crude acetic acid product to obtain acetic acid and a PRC stream comprising one or more PRC's and methyl iodide;
   extracting the PRC stream with water to form a raffinate containing methyl iodide and an aqueous extract stream containing said one or more PRC's;
   hydrogenating the acetic acid in a hydrogenation system in the presence of a hydrogenation catalyst to form a crude ethanol product comprising ethanol and water;
   separating the ethanol from the water in the crude ethanol product to form an ethanol stream and a water stream; and
   using at least a portion of the water stream in the extracting step.

* * * * *